US008324561B2

(12) United States Patent
Iguchi et al.

(10) Patent No.: US 8,324,561 B2
(45) Date of Patent: Dec. 4, 2012

(54) PHOTODETECTOR AND JIG FOR SAMPLE HOLDER

(75) Inventors: Kazuya Iguchi, Hamamatsu (JP); Kengo Suzuki, Hamamatsu (JP)

(73) Assignee: Hamamatsu Photonics K.K., Hamamatsu-shi, Shizuoka (JP)

(*) Notice: Subject to any disclaimer, the term of this patent is extended or adjusted under 35 U.S.C. 154(b) by 554 days.

(21) Appl. No.: 12/529,253

(22) PCT Filed: Mar. 1, 2007

(86) PCT No.: PCT/JP2007/053947
§ 371 (c)(1),
(2), (4) Date: Sep. 30, 2009

(87) PCT Pub. No.: WO2008/107947
PCT Pub. Date: Sep. 12, 2008

(65) Prior Publication Data
US 2010/0108869 A1    May 6, 2010

(51) Int. Cl.
*G01J 1/04* (2006.01)
*G01N 21/01* (2006.01)
*G01N 21/63* (2006.01)
(52) U.S. Cl. .................. 250/228; 356/236; 356/246
(58) Field of Classification Search .................. 250/228; 356/236, 244, 246
See application file for complete search history.

(56) References Cited

U.S. PATENT DOCUMENTS

| | | | | |
|---|---|---|---|---|
| 2,707,900 A | * | 5/1955 | Maresh et al. ............... | 356/246 |
| 3,838,926 A | | 10/1974 | Kato et al. | |
| 4,012,144 A | * | 3/1977 | Hedelman .................... | 356/73 |
| 4,583,860 A | * | 4/1986 | Butner ........................ | 356/446 |
| 4,942,305 A | * | 7/1990 | Sommer ...................... | 250/574 |
| 6,061,140 A | * | 5/2000 | Berg et al. ................... | 356/418 |
| 6,188,475 B1 | * | 2/2001 | Inman et al. ................. | 356/246 |
| 2010/0108869 A1 | * | 5/2010 | Iguchi et al. ................. | 250/228 |

FOREIGN PATENT DOCUMENTS

| | | |
|---|---|---|
| JP | 52-36081 | 3/1977 |
| JP | 52-37986 | 3/1977 |
| JP | 53-016387 | 4/1978 |
| JP | 54-35114 | 3/1979 |

(Continued)

OTHER PUBLICATIONS

K. Koike et al., "A Simple Integrating-Sphere Fluorometer for Monitoring the Growth of Benthic Microalgae," La Mer, 32, 1994, Societe Franco-Japonaise D'Oceanographie, Tokyo, pp. 45-50.

*Primary Examiner* — John Lee
(74) *Attorney, Agent, or Firm* — Drinker Biddle & Reath LLP

(57) ABSTRACT

A photodetecting device 1 includes an integrating sphere 20 for observing light to be measured generated according to irradiation of a sample with excitation light and a sample holder 60 removably attached to the integrating sphere 20, the integrating sphere 20 has an excitation light introducing hole 201 for introducing the excitation light and a sample introducing hole 205 for introducing a cell C held by the sample holder 60, the sample holder 60 is locked to the sample introducing hole 205 and holds the cell C for accommodating the sample, and the cell is disposed so that an entrance surface of the cell C, through which the excitation light enters the cell C, inclines relative to the surface perpendicular to the optical axis L of the excitation light.

13 Claims, 14 Drawing Sheets

FOREIGN PATENT DOCUMENTS

| | | |
|---|---|---|
| JP | 55-038616 | 10/1980 |
| JP | 3-248045 | 11/1991 |
| JP | 5-005288 | 1/1993 |
| JP | 5-113386 | 5/1993 |
| JP | 2517102 | 4/1996 |
| JP | 2811565 | 8/1998 |
| JP | 2002243642 | 8/2002 |
| JP | 2003-215041 | 7/2003 |
| JP | 2007-33334 | 2/2007 |
| JP | 2007-86031 | 4/2007 |

* cited by examiner

Fig.7
(a)
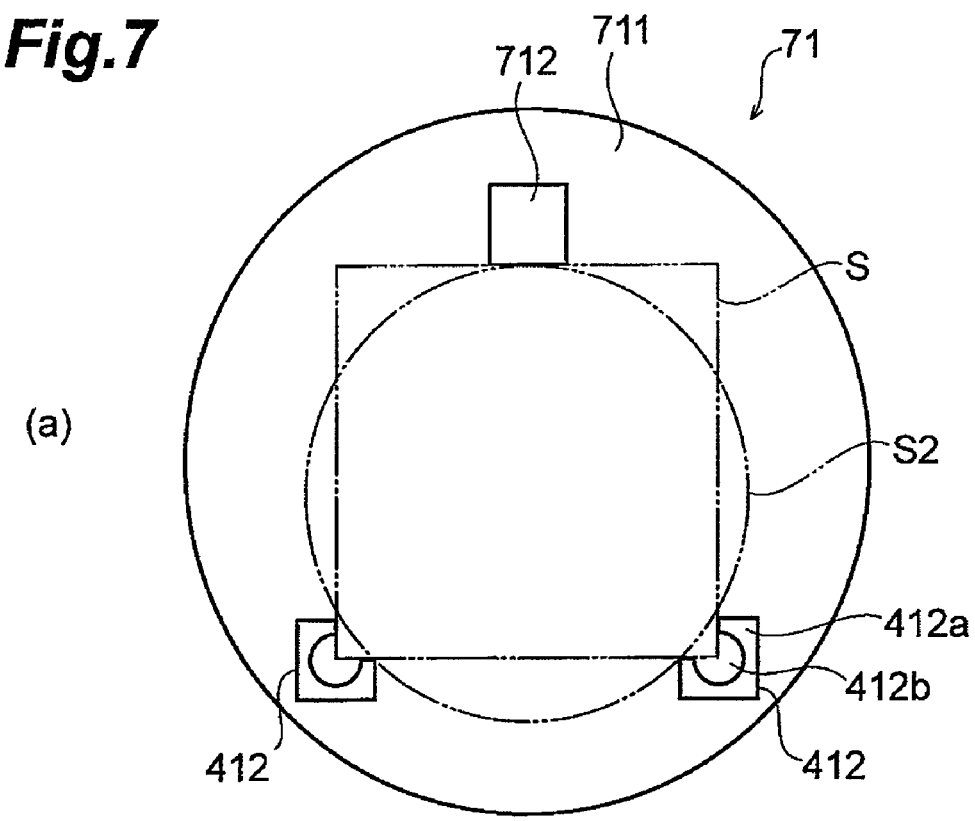
(b)
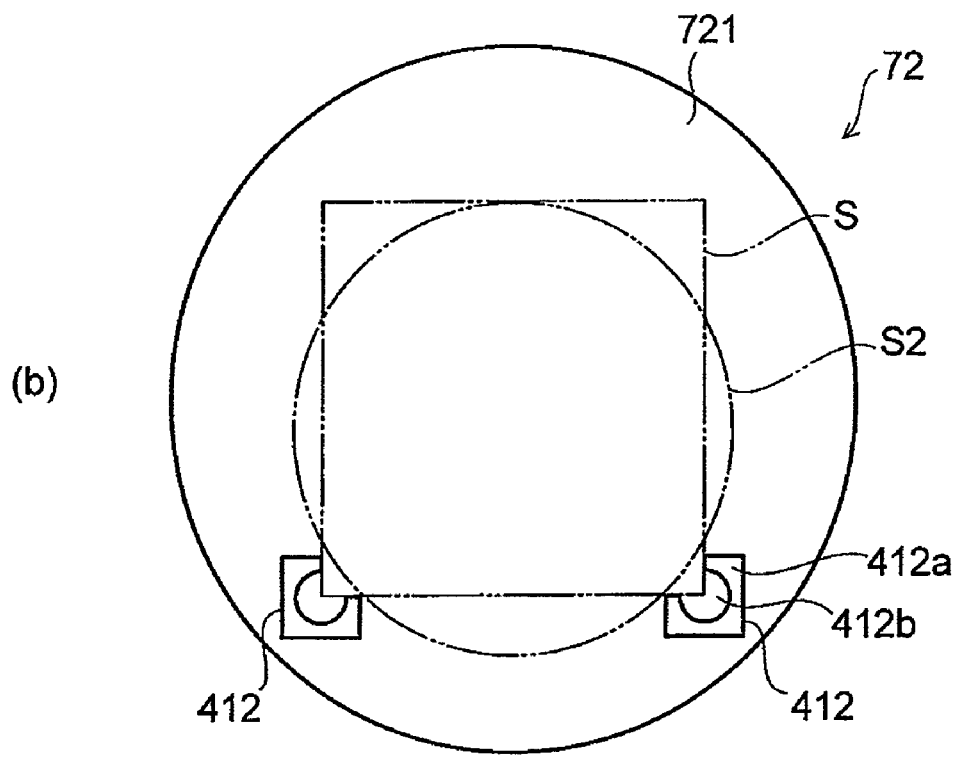

PHOTODETECTOR AND JIG FOR SAMPLE HOLDER

TECHNICAL FIELD

The present invention relates to a photodetecting device which includes an integrating sphere for observing light to be measured generated according to irradiation of a sample with excitation light and a sample holder to be removably attached to the integrating sphere, and a jig for a sample holder for attaching a cell to the sample holder.

BACKGROUND ART

An integrating sphere is used for measuring the intensity of light to be measured when the light to be measured is generated radially. A high-diffuse reflecting powder is coated on a spherical main body inner wall of the integrating sphere, and when the light to be measured is generated radially, it is multiply diffused and reflected by the high-diffusion reflecting powder. This diffuse-reflected light enters a photodetector, and an output signal of the photodetector is led to a light intensity meter, and thus the intensity of the emitted light to be measured can be measured. Such an integrating sphere is disclosed in Patent Documents 1 to 3 listed below.

Patent Document 1: Japanese Patent Publication No. 2517102
Patent Document 2: Japanese Patent Publication No. 2811565
Patent Document 3: Japanese Patent Publication No. S54-35114

DISCLOSURE OF THE INVENTION

Problems to be Solved by the Invention

The integrating sphere disclosed in Patent Documents 1 to 3 listed above includes a reaction tube called a cell disposed inside the integrating sphere for measuring light to be measured from a solution in the cell. When light to be measured from a solution in the cell is measured in the conventional integrating sphere as illustrated in Patent Documents 1 to 3, there is a case that the intensity of the light to be measured cannot always be accurately measured.

Therefore, an object of the present invention is to provide a photodetecting device for accurately measuring light to be measured from a sample accommodated in the cell, and a jig for sample holder for attaching the cell to a sample holder to be used in the photodetecting device.

Means for Solving the Problems

The inventors of the present invention repeatedly examined the reason why the intensity of light to be measured could not always be accurately measured in the conventional integrating sphere. When a sample accommodated in the cell is irradiated with excitation light, light to be measured is generated from the sample. Generally, this generated light to be measured contains at least one of a reflected component of the excitation light and a component generated from the sample which has absorbed the excitation light (for example, when either one component is filtered, the light to be measured is composed of the other component). The inventors found that excitation light was introduced into the integrating sphere and irradiated the sample, and light to be measured generated according to the irradiation returned to a hole for entrance of excitation light formed in the integrating sphere under certain conditions. The present invention was made based on these findings.

A photodetecting device according to the present invention includes an integrating sphere for observing light to be measured generated according to irradiation of a sample with excitation light, and a sample holder to be removably attached to the integrating sphere, and the integrating sphere has an excitation light introducing hole for introducing excitation light and a sample introducing hole for introducing a cell held by the sample holder, and the sample holder is locked to the sample introducing hole, and has a holding part which holds the cell for accommodating the sample and positioning means for disposing the cell so that an entrance surface of the cell, through which the excitation light enters the cell, inclines relative to a surface perpendicular to the optical axis of the excitation light.

According to the present invention, a sample holder by which an entrance surface of a cell accommodating a sample can be disposed so as to incline with respect to the optical axis of excitation light is removably attached to the integrating sphere; so that the cell can be held at an angle corresponding to the shape of the cell with respect to the optical axis of the excitation light. Therefore, setting can be made to prevent measured light generated by irradiating the sample with excitation light from returning to the excitation light introducing hole.

Further, in the present invention, it is also preferable that the holding part includes a grip portion for gripping the cell, and the grip portion includes a buffering member at a portion which comes into contact with the cell. The grip portion having the buffering member at a portion which comes into contact with the cell holds the cell, so that the cell can be held without being damaged.

In the present invention, it is also preferable that the positioning means is a locking part for locking the sample holder to the integrating sphere. The locking part such as a positioning pin which locks the sample holder to the integrating sphere functions as positioning means for disposing the cell so that the entrance surface of the cell for entering the excitation light into the cell inclines from a surface perpendicular to the optical axis of the excitation light, so that the sample holder is easily attached and removed.

A jig for sample holder according to the present invention adjusts a relative positional relationship between a cell which is introduced to the inside of an integrating sphere for observing light to be measured generated according to irradiation of a sample with excitation light, and a sample holder which is removably attached into a sample introducing hole formed in the integrating sphere and holds the cell, and includes: a main body part extending along the cell; a holder holding part which is formed at the main body part and holds the sample holder; and angle setting means which is formed at the main body part and directs an entrance surface of the cell through which the excitation light enters the cell in a predetermined direction with respect to the sample holder.

According to the present invention, while the sample holder is held, the cell directed in a predetermined direction with respect to the sample holder can be disposed. In this disposed state, by holding the cell by the sample holder, the cell can be held in a predetermined positional relationship with the sample holder. Therefore, the sample holder holding the cell can be attached to the integrating sphere, and the entrance surface of the cell can be held at a predetermined angle with respect to the optical axis of the excitation light.

In the present invention, it is also preferable that the angle setting means is a hole having substantially the same shape as the sectional shape of the cell, formed at a cell holding part extending so as to intersect with the main body part. The cell is directed by a hole having substantially the same shape as the sectional shape of the cell, so that the cell can be easily and accurately directed.

In the present invention, it is also preferable that the angle setting means is a mark provided at a predetermined position at which the cell is visible. A mark is provided at a position at which the cell is visible, so that the angle of the cell with respect to the sample holder can be adjusted to and held at the mark.

In the present invention, it is also preferable that height adjusting means is further provided for matching the position of the optical axis of the excitation light inside the integrating sphere and the entrance position of the excitation light on the cell. The position of the optical axis of the excitation light and the entrance position on the cell can be matched and held, so that the sample accommodated inside the cell can be accurately irradiated with the excitation light.

A photodetecting device according to the present invention includes an integrating sphere for observing light to be measured generated according to irradiation of a sample with excitation light; and a sample holder to be removably attached to the integrating sphere, and the integrating sphere has an excitation light introducing hole for introducing excitation light; a first sample introducing hole for introducing a first sample holder; and a second sample introducing hole for introducing a second sample holder, the first sample holder has a holding part which holds a cell for accommodating a sample; and a first locking part for locking the first sample holder to the integrating sphere, the second sample holder has a sample stage onto which a sample is placed; and a second locking part for locking the second sample holder to the integrating sphere, and the first sample introducing hole is formed at a position on a meridian having poles set at a position at which the excitation light introducing hole is formed and a position at which the second sample introducing hole is formed, and at distances substantially equal to each other from the poles of the meridian.

According to the present invention, the first sample holder and the second sample holder are provided, and the first sample introducing hole is provided between the excitation light introducing hole and the second sample introducing hole, so that the first sample holder can be disposed between the excitation light introducing hole and the second sample holder. Therefore, by disposing the first sample holder while the second sample holder is left attached to the integrating sphere, light to be measured from a sample held by the first sample holder can be observed. Further, by disposing the second sample holder while the first sample holder is left attached to the integrating sphere, light to be measured from a sample held by the second sample holder can be observed.

In the present invention, it is also preferable that the first locking part has positioning means for disposing the cell so that an entrance surface of the cell, through which the excitation light enters the cell, inclines relative to a surface perpendicular to the optical axis of the excitation light. The cell is disposed so as to incline from the surface perpendicular to the optical axis of the excitation light, so that the excitation light can be restrained from returning to the excitation light introducing hole.

In the present invention, it is also preferable that a placing surface on which the sample is placed is formed on the sample stage so as to incline relative to a surface perpendicular to the optical axis of the excitation light, and the second locking part locks the second sample holder to the integrating sphere so that the placing surface is directed in a predetermined direction inside the integrating sphere. The placing surface is formed so as to incline from the surface perpendicular to the optical axis of the excitation light, so that the excitation light can be restrained from returning to the excitation light introducing hole.

In the present invention, it is also preferable that a portion to be exposed inside the integrating sphere of at least one of the first sample holder and the second sample holder is a diffuse reflecting surface. The portions to be exposed inside the integrating sphere of the first sample holder and the second sample holder are covered by a diffuse reflecting agent, so that when a sample held by one sample holder is observed in a state where the first sample holder and the second sample holder are attached to the integrating sphere, the portion covered by the diffuse reflecting agent of the other sample holder can be made to function as a part of the integrating sphere inner wall.

In the present invention, it is also preferable that the integrating sphere is attached to an L-shaped mount having two placing surfaces. The integrating sphere is attached to the L-shaped mount, so that the angle of holding the integrating sphere can be changed by 90 degrees, and the integrating sphere can be set lengthwise and sideways. Therefore, for example, when the second sample holder is used, the integrating sphere can be set lengthwise, and when the first sample holder is used, the integrating sphere can be set sideways.

Effects of the Invention

According to the present invention, setting can be made so as to prevent light to be measured generated according to irradiation of a sample with excitation light from returning to the excitation light introducing hole. Therefore, light to be measured from the sample accommodated in the cell can be more accurately measured.

BRIEF DESCRIPTION OF THE DRAWINGS

FIG. 7 shows plan views showing an exemplary variation of the placing surface.

DESCRIPTION OF THE SYMBOLS

Figure 1:
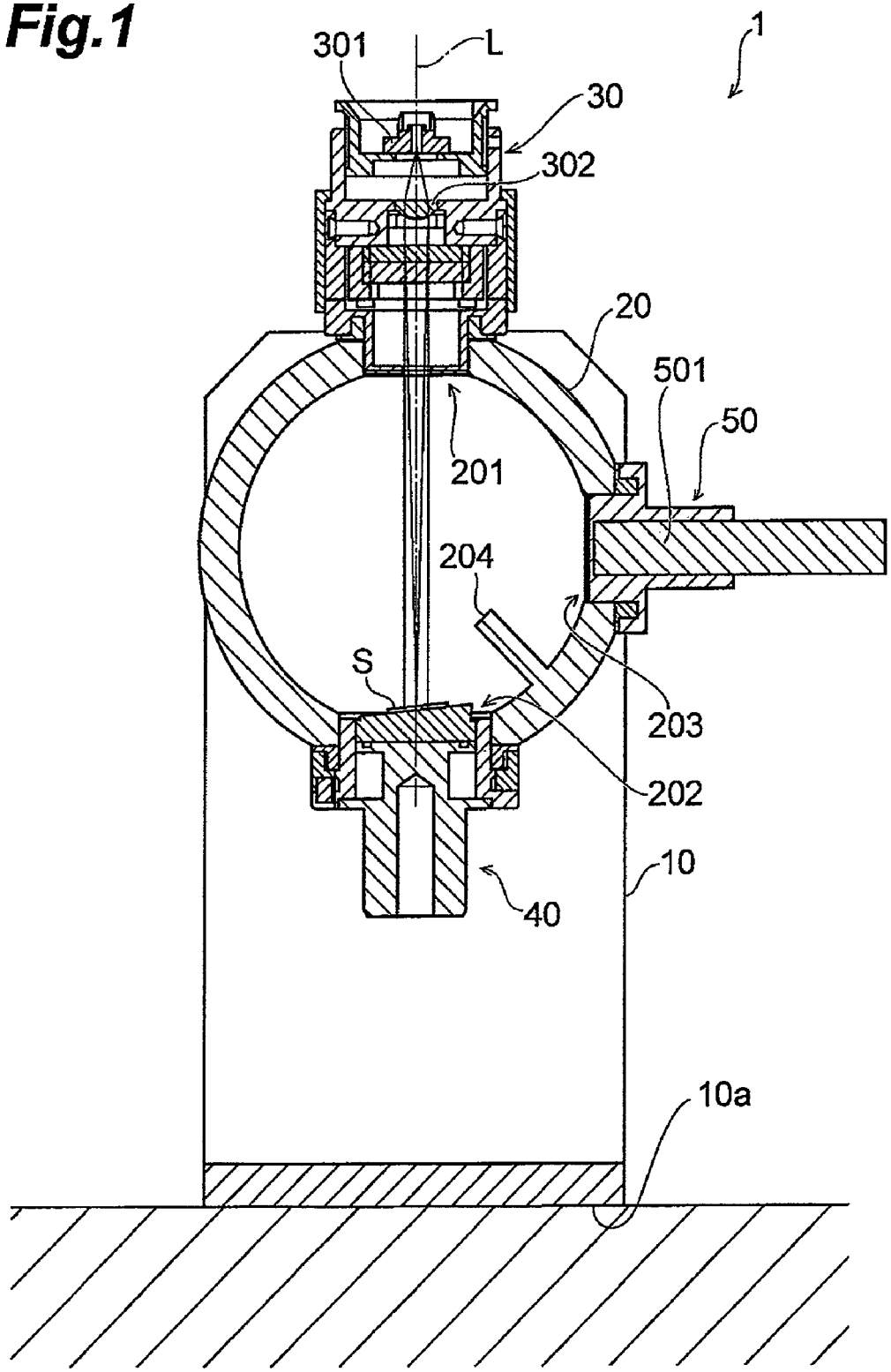
FIG. 1 is a sectional view showing a photodetecting device of the present embodiment.

1—photodetecting device, 10—mount, 20—integrating sphere, 30—optical fiber holder for excitation light, 40, 60—sample holder, 50.

BEST MODES FOR CARRYING OUT THE INVENTION

The findings of the present invention can be easily understood by considering the following detailed description with reference to the attached drawings shown only for illustration. Subsequently, an embodiment of the present invention will be described with reference to the attached drawings. If possible, portions identical to each other are attached with the same reference numerals and letters, and overlapping description will be omitted.

Figure 2:
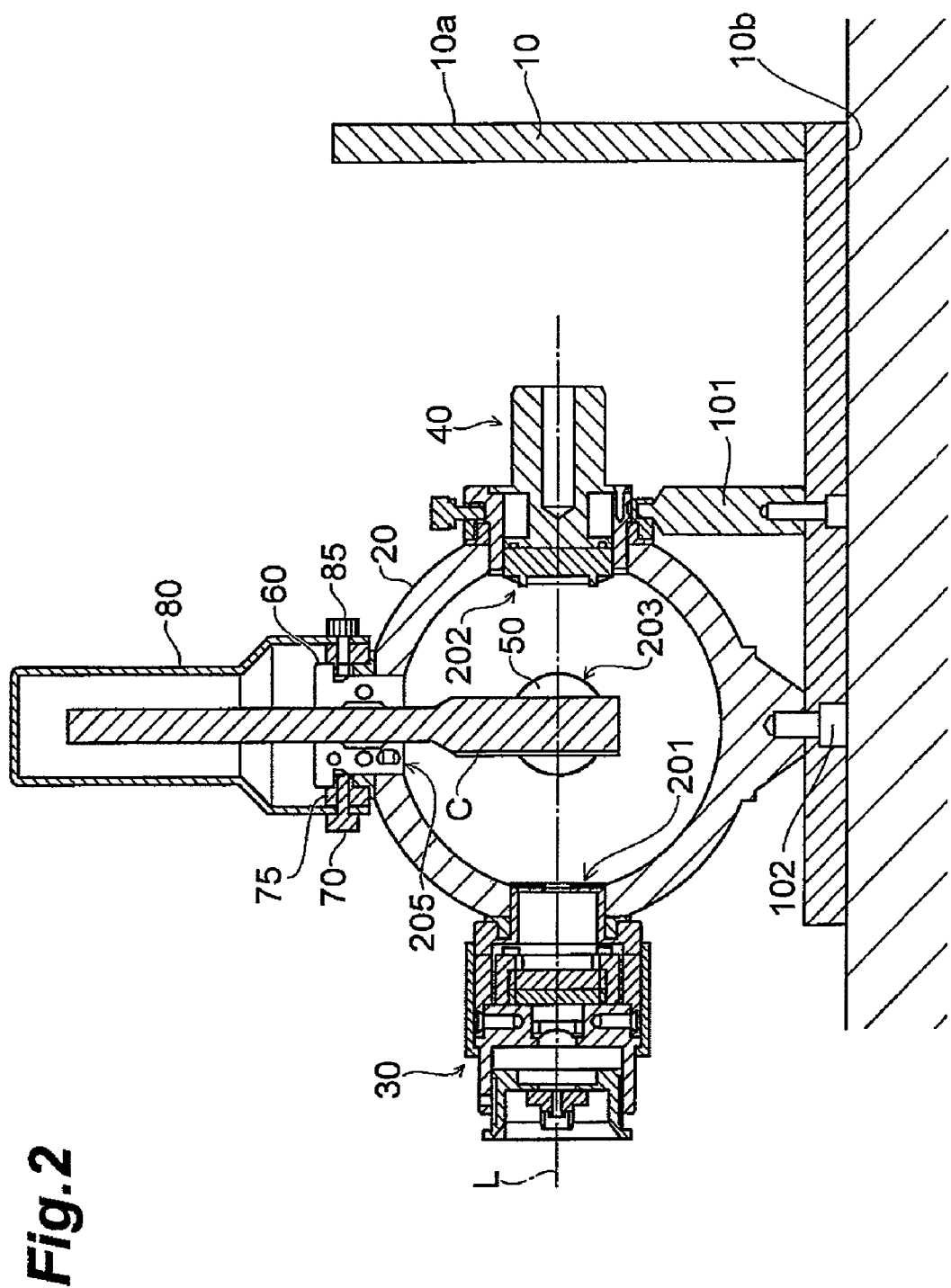
FIG. 2 is a sectional view showing a photodetecting device of the present embodiment.

A photodetecting device of an embodiment of the present invention will be described with reference to FIG. 1 and FIG. 2. FIG. 1 is a view showing a section along the excitation light optical axis L of the photodetecting device 1 of the present embodiment. FIG. 2 is a view showing a section orthogonal to the section of FIG. 1, along the excitation light optical axis L. FIG. 1 shows a case where the photodetecting device 1 is stood so that the excitation light optical axis L is along the vertical line, and a sample held by the sample holder 40 (second sample holder) is measured. On the other hand, FIG. 2 shows a case where the photodetecting device 1 is laid down so that the excitation light optical axis L is along the horizontal line and a sample held by the sample holder 60 (first sample holder) is measured.

The photodetecting device 1 includes an integrating sphere 20 for observing light to be measured generated according to irradiation of a sample with excitation light; sample holders 40 and 60 which are removably attached to the integrating sphere 20 and selectively used; an optical fiber holder 30 for excitation light for introducing the excitation light into the integrating sphere 20; an optical fiber holder 50 for photodetection for acquiring light to be measured; and an L-shaped mount 10 having two placing surfaces 10a and 10b. The integrating sphere 20 is attached to the mount 10 by an attaching screw 102.

First, with reference to FIG. 1, a configuration of the photodetecting device 1 in a case where the photodetecting device 1 is stood and disposed while the placing surface 10a of the mount 10 is positioned downward so that the excitation light optical axis L is along the vertical line, and a sample held by the sample holder 40 is measured, will be described. Here, the sample holder 40 is used mainly for measurement of a solid sample and a powder sample, etc., and these samples may be held by the sample holder 40 while being coated on a substrate such as a glass, or may be held by the sample holder 40 while being accommodated in a container such as a petri dish.

In the integrating sphere 20, an excitation light introducing hole 201, a sample introducing hole 202 (second sample introducing hole), and a photodetector introducing hole 203 are formed. The excitation light introducing hole 201 is formed at one (the upper pole in FIG. 1) of the poles at which the integrating sphere 20 and the vertical line (vertical line in the state of FIG. 1) intersect with each other. The sample introducing hole 202 is formed at the other pole (the lower pole in FIG. 1) opposite to the excitation light introducing hole 201. The photodetector introducing hole 203 is formed at a position on the meridian having poles set at the position at which the excitation light introducing hole 201 is formed and the position at which the sample introducing hole 202 is formed, and at distances equal to each other from the poles of the meridian. A light-shielding plate 204 is formed between the sample introducing hole 202 and the photodetector introducing hole 203.

An optical fiber holder 30 for excitation light is attached into the excitation light introducing hole 201, a sample holder 40 is attached into the sample introducing hole 202, and an optical fiber holder 50 for photodetection is attached into the photodetector introducing hole 203.

An optical fiber (not shown) attached to a fiber holding part 301 of the optical fiber holder 30 for excitation light is connected to an excitation light source not shown. Excitation light emitted from the excitation light source (not shown) is guided to a lens 302 of the optical fiber holder 30 for excitation light through the optical fiber (not shown). The excitation light is guided into the integrating sphere 20 along the optical axis L and irradiated onto a sample S placed on the sample holder 40 disposed opposite to the optical fiber holder 30 for excitation light.

When the sample S is irradiated with the excitation light, light to be measured composed of a reflected component of the excitation light and a component generated from the sample S which has absorbed the excitation light is generated. Light to be measured from the sample S irradiated with the excitation light is multiply diffused and reflected by a diffuse reflecting agent such as barium sulfate coated on the inner wall of the integrating sphere 20. This diffuse-reflected light to be measured enters the optical fiber 501 attached to the optical fiber holder 50 for photodetection. The optical fiber 501 is connected to a photodetector which is not especially limited but is, for example, a multi-channel photodetector (not shown). Therefore, light to be measured which has entered the optical fiber 501 is guided to the multi-channel photodetector (not shown) through the optical fiber 501. Measurement data detected by the multi-channel photodetector (not shown) is output to a data processor (not shown) and processed, and the intensity of the light to be measured is measured. In the present embodiment, the photodetector is used upon being connected to the optical fiber 501, however, the photodetector such as a photoelectric conversion element may be directly attached into the photodetector introducing hole 203. In the present description, the photodetector is used upon being regarded as including both of these forms.

The light-shielding plate 204 is provided to prevent the light to be measured from the sample S from directly entering the optical fiber 501. This is because remarkable errors occur in the intensity data of the light to be measured if light to be measured directly enters the optical fiber 501. Preferably, the light-shielding plate 204 is formed at a position at substantially equal distances from the photodetector introducing hole 203 and the sample introducing hole 202 and on a meridian passing through the photodetector introducing hole 203 when the position at which the excitation light introducing hole 201 is formed and the position at which the sample introducing hole 202 is formed are set as poles of the meridian. A baffle for preventing the light to be measured from the sample from directly entering the optical fiber 501 may also be attached to the optical fiber 50 for photodetection. In this case, the baffle may project inside the integrating sphere, and the baffle may be coated with a diffuse reflecting agent such as barium sulfate, or may further be formed by shaping a diffuse reflecting material. Disposition of the baffle is especially preferable in measurement using the cell C as a sample container.

Figure 3:
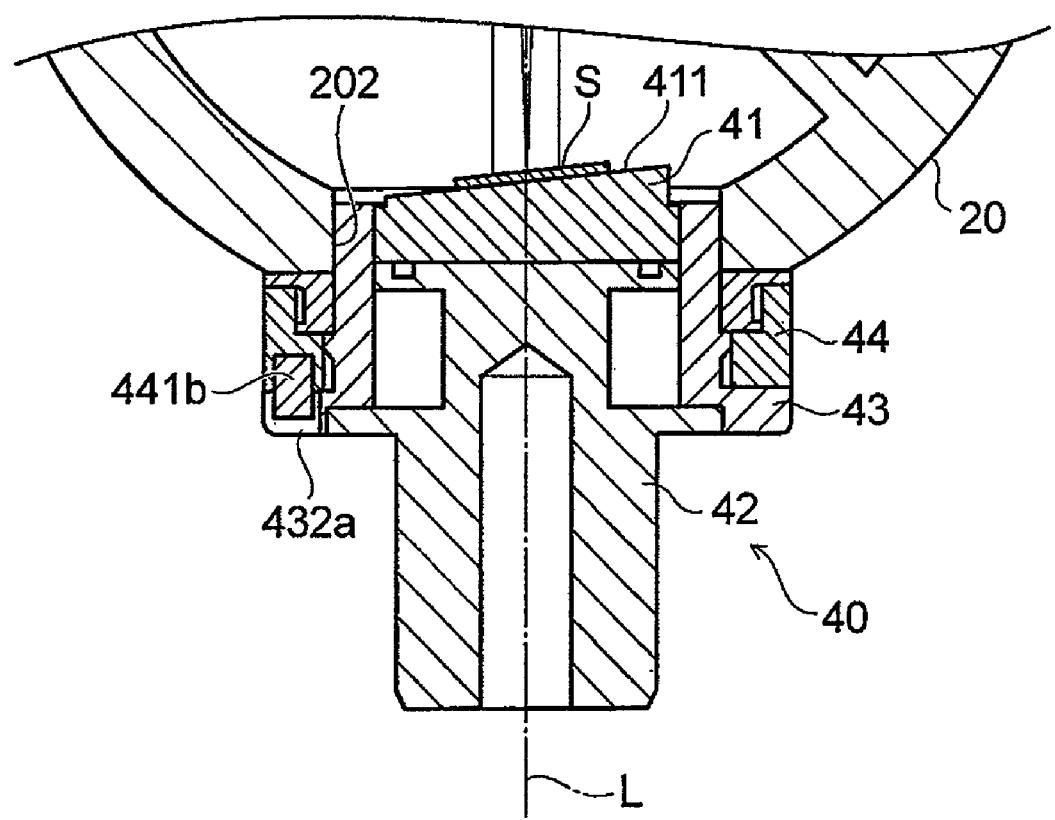
FIG. 3 is an enlarged sectional view of FIG. 1.
Figure 4:
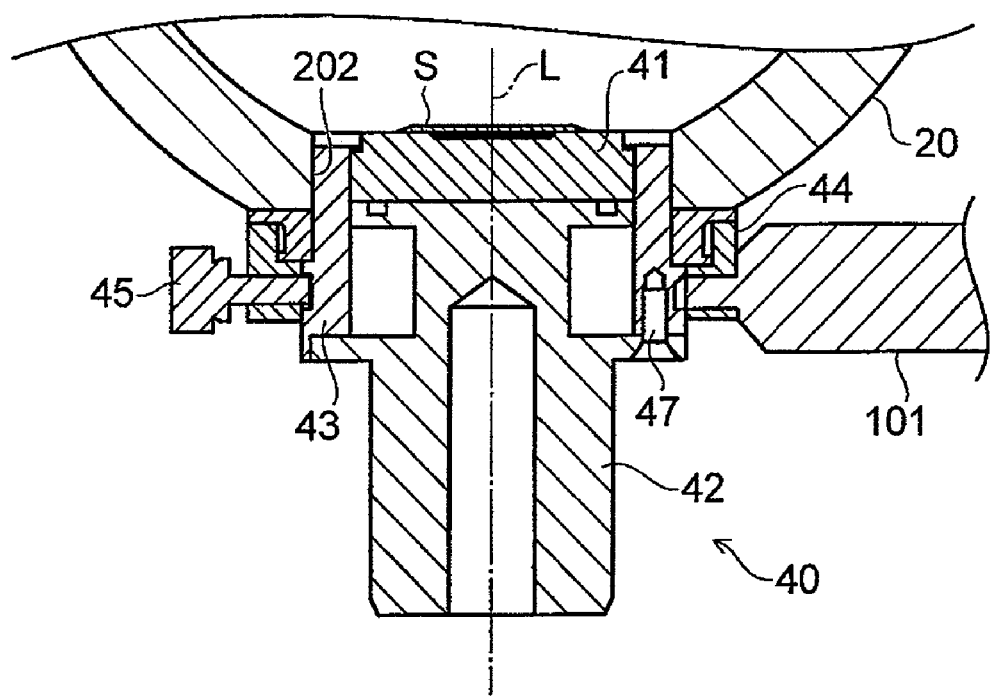
FIG. 4 is an enlarged sectional view of FIG. 2.

Subsequently, the sample holder 40 will be described with reference to FIG. 3 and FIG. 4. FIG. 3 is an enlarged sectional view of the vicinity of the sample holder 40 in FIG. 1. FIG. 4 is an enlarged sectional view of the vicinity of the sample holder 40 in FIG. 2.

The sample holder 40 includes a sample stage 41, a handling knob 42, a holder main body 43, and an attaching flange 44 (locking part). A sample S is placed on a placing surface 411 of the sample stage 41. The placing surface 411 to be exposed inside the integrating sphere is preferably coated with a diffuse reflecting agent such as barium sulfate, and this will be described later. As shown in FIG. 3, the placing surface 411 is formed so as to incline relative to a surface perpendicular to the optical axis L of the excitation light. The sample stage 41 is held between the holder main body 43 and the handling knob 42. The holder main body 43 to which the sample stage 41 and the handling knob 42 are attached is inserted into the attaching flange 44. As shown in FIG. 4, into the attaching flange 44, a fixing projection 101 extending from the mount 10 is inserted, and on the side opposite to the inserted portion, a fixation screw 45 is provided. When tightening the fixation screw 45, the holder main body 43 is sandwiched and fixed between the fixing projection 101 and the fixation screw 45.

Figure 5:
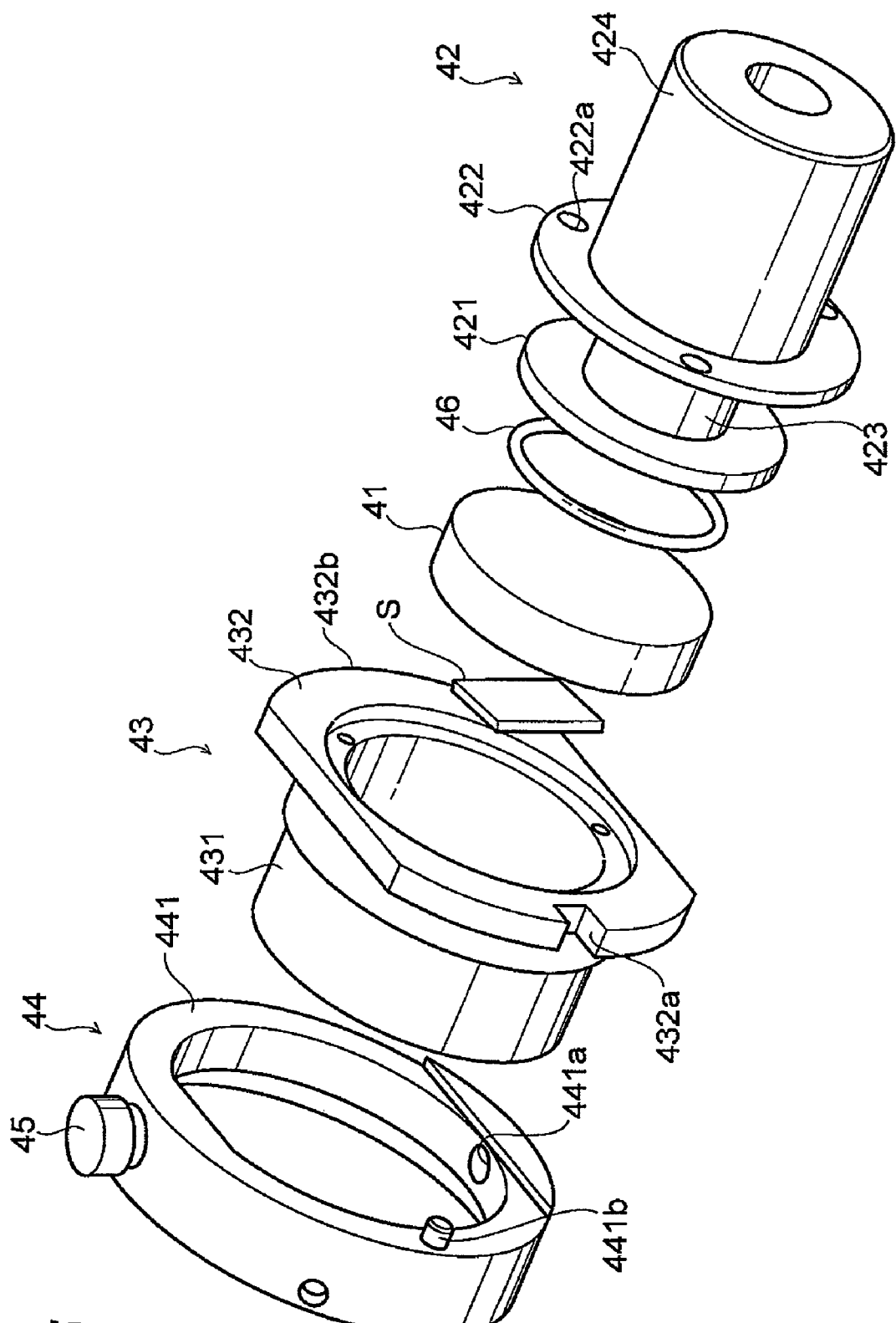
FIG. 5 is an exploded perspective view of a sample holder.

The sample holder 40 will further be described in detail. FIG. 5 is an exploded perspective view of the sample holder 40. The holder main body 43 has a cylindrical tubular part 431 and a flange part 432 provided on one end of the tubular part 431. In the flange part 432, a positioning notch 432a is formed. In the flange part 432, screw holes 432b for attaching the handling knob 42 are formed. On the other end of the tubular part 431, a folded-back portion not shown is formed, and the sample stage 41 is sandwiched and fixed between the folded-back portion and the handling knob 42.

The handling knob 42 includes a first flange part 421, a second flange part 422, a small-diameter part 423, and a large-diameter part 424. The small-diameter part 423 is cylindrical, and is formed between the first flange part 421 and the second flange part 422. The large-diameter part 424 is cylindrical, and is formed so as to extend to the side opposite to the small-diameter part 423 from the second flange part 422. The first flange part 421 is a part for sandwiching and fixing the sample stage 41 in combination with the holder main body 43. In the second flange part 422, holes 422a are formed at positions corresponding to the screw holes 432 of the holder main body 43. Therefore, when the sample stage 41 is sandwiched and the holder main body 43 and the handling knob 42 are screwed, the sample stage 41, the holder main body 43, and the handling knob 42 can be fixed to each other. An O-ring 46 is provided between the sample stage 41 and the handling knob 42, so that the sample stage 41 can be prevented from turning with respect to the handling knob 42.

In the sample holder 40 shown in FIG. 5, the sample stage 41 is sandwiched and held between the holder main body 43 and the handling knob 42, however, it is not limited to this configuration. For example, the sample stage 41 made of a diffuse reflecting material may be screwed and held from the handling knob 42 side of the holder main body 43. With this configuration, it becomes unnecessary to provide a folded-back portion on the other end of the tubular part 431, and as a result, the area of the sample stage 41 to be exposed inside the integrating sphere can be more largely secured. With this configuration, even when the sample stage 41 is contaminated by a sample, the sample stage 41 is easily replaced. The sample stage 41 may be fixed with screws and positioned by using a positioning pin.

The attaching flange 44 includes a flange main body 441 and a fixation screw 45. On the flange main body 441, a positioning pin 441b is provided. The positioning pin 441b is provided at a position corresponding to the positioning notch 432a of the holder main body 43. Therefore, when the tubular part 431 of the holder main body 43 is inserted into the flange main body 441, the positioning pin 441b is inserted into the positioning notch 432a, and the holder main body 43 is positioned with respect to the flange main body 441. On the side opposite to the position at which the fixation screw 45 is provided, a fixation hole 441a is formed. The fixation hole 441a is a hole into which the fixing projection 101 described above is inserted.

Figure 6:
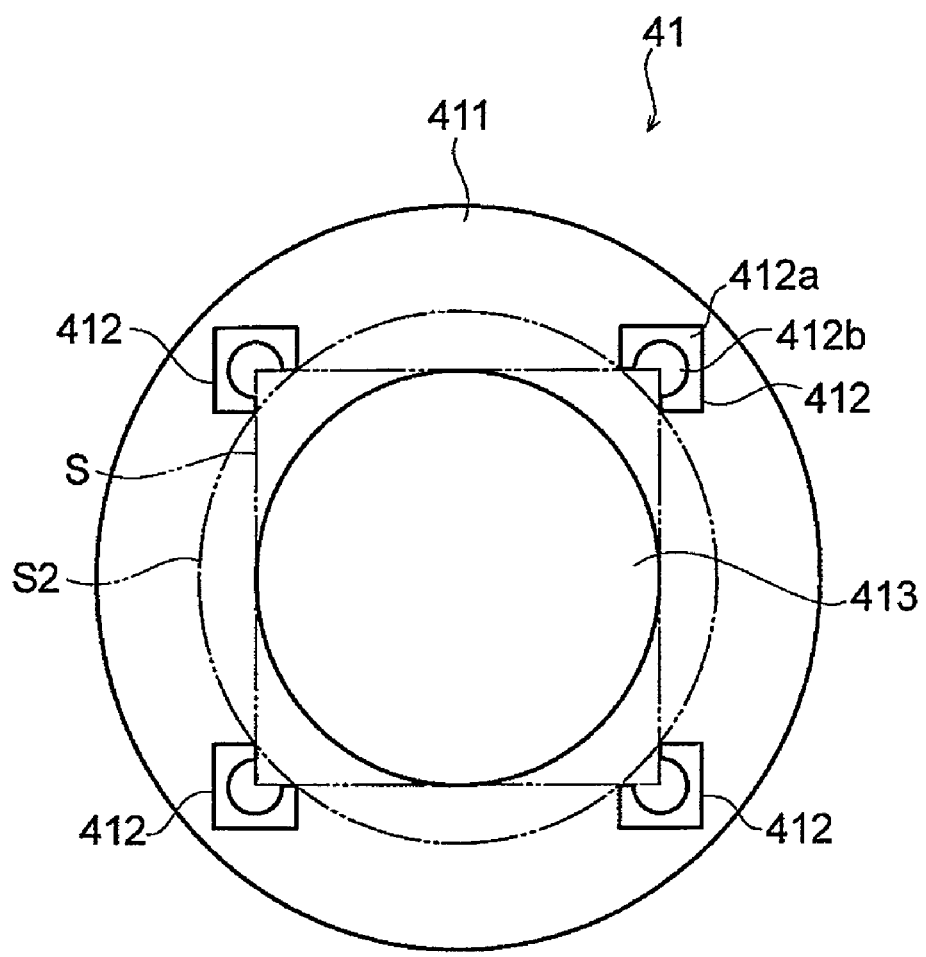
FIG. 6 is a plan view showing a placing surface of the sample holder.

The sample stage 41 will be described with reference to FIG. 6. FIG. 6 is a plan view of the sample stage 41 as viewed from the placing surface 411 side. In FIG. 6, the upper side of the drawing is a portion at which the placing surface 411 becomes higher, and the lower side of the drawing is a portion at which the placing surface 411 becomes lower. On the placing surface 411, positioning portions 412 are formed at four positions. On the placing surface 411 inward of the positioning portions 412 formed at the four positions, a recess 413 is formed.

The positioning portions 412 are mutually arranged at even intervals near the outer periphery of the circular placing surface 441. Each positioning portion 412 includes a raised portion 412a and a recessed portion 412b surrounded by the raised portion 412a. The positioning portion 412 is formed by forming a prismatic protrusion, with a columnar hole at the center of the prismatic protrusion, and cutting one corner of the prismatic protrusion. The cut portion of each positioning portion 412 is formed so as to be toward the center of the placing surface 411.

Therefore, when the sample S is rectangular as shown in the drawing, four corners of the sample S enter the recessed portions 412b of the positioning portions 412, and held by the raised portions 412a. When the sample is put into a holding member S2 such as a circular petri dish, similar to the rectangular sample, the holding member S2 is held by the positioning portions 412 formed at the four corners.

When the sample S is formed by coating a luminescence material on a rectangular glass substrate, a part of photons emitted from the luminescence material propagates in the glass substrate as an optical waveguide, and is emitted from the end face of the glass substrate. Therefore, when the form of the positioning portions 412 of the present embodiment is adopted, the contact portion between the sample S and the positioning portion 412 can be made smaller, and photons emitted from the end face of the sample S can be measured with higher accuracy.

Even when a luminescence material adheres to the placing surface 411 side of the sample S, the recess 413 is formed on the placing surface 411, so that adhesion of the luminescence material to the placing surface 411 can be suppressed. The recessed portion 412b is also provided on the positioning portion 412, so that the adhesion of the luminescence material to the positioning portion 412 can also be suppressed.

An exemplary variation of the positioning portions 412 is shown in FIG. 7. The sample stage 71 shown in (a) in FIG. 7 includes a pair of positioning portions 412 and one protrusion 712 formed on the placing surface 711. The pair of positioning portions 412 and the protrusion 712 are mutually disposed at even intervals near the outer periphery of the circular placing surface 441.

In the sample stage 72 shown in (b) in FIG. 7, a pair of positioning portions 412 are formed on the placing surface 721. The pair of positioning portions 412 are provided at positions corresponding to two lower positioning portions of the four positioning portions 412 of FIG. 6. The placing surface 721 inclines so as to become higher at the upper side of the drawing and become lower at the lower side of the drawing, so that the sample S (holding member S2) can be held by the two positioning portions 412.

Figure 8:
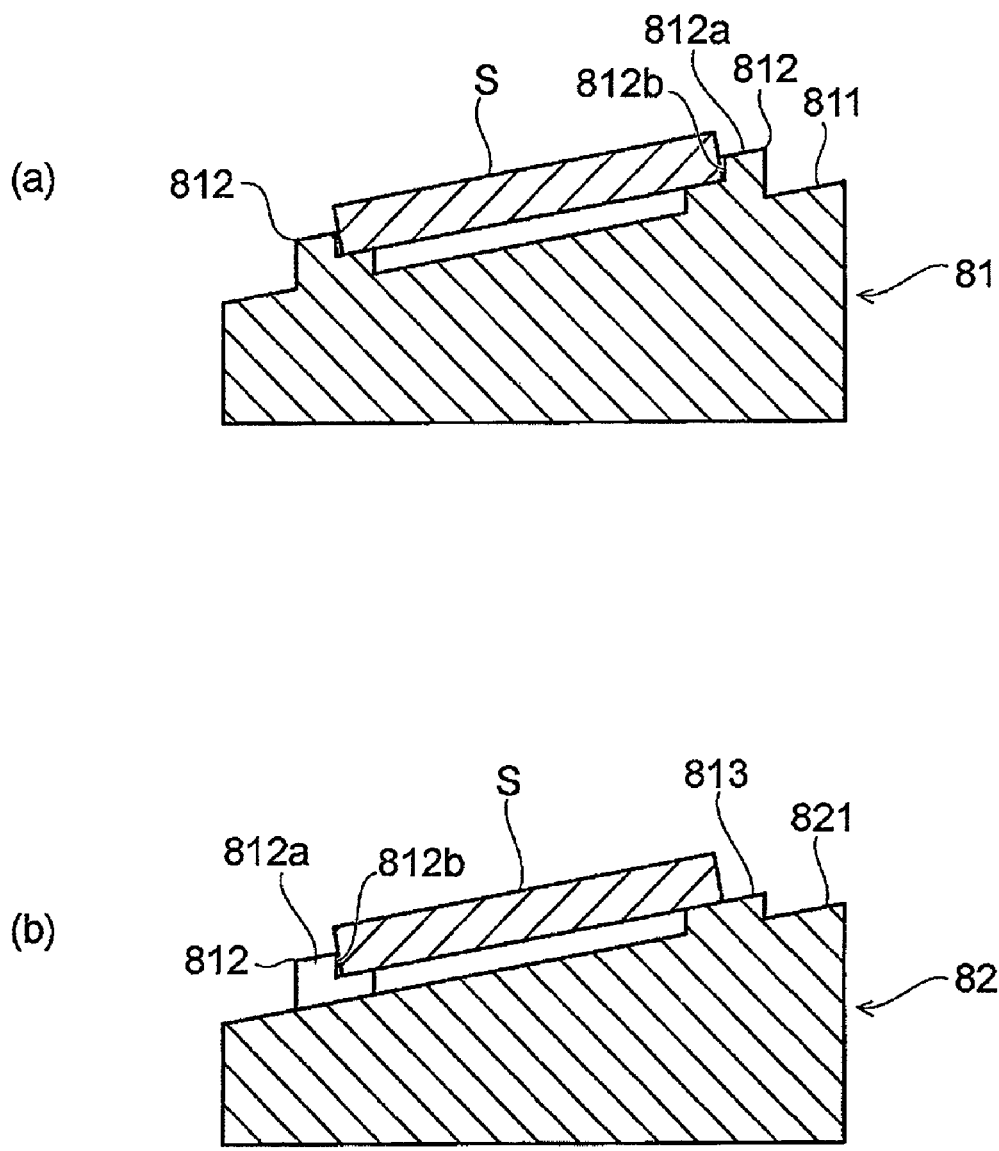
FIG. 8 shows sectional views showing an exemplary variation of a sample stage.

Other than the form in which the recess 413 is formed on the placing surface 411 as described above with reference to FIG. 6, there is a way to prevent the sample S from coming into contact with the placing surface 411. An example will be described with reference to FIG. 8. FIG. 8 shows sectional views of a sample stage showing the example.

The example shown in (a) in FIG. 8 shows a sample stage 81 formed by changing the shape of the positioning portions 412 at the four positions of the sample stage 41 described with reference to FIG. 6. FIG. 8(a) is a sectional view of the vicinity of the positioning portion 812 formed on the placing surface 811 of the sample stage 81. As shown in (a) in FIG. 8, the positioning portion 812 has a raised portion 812a and a recessed portion 812b surrounded by the raised portion 812a. The recessed portion 812b is recessed with respect to the raised portion 812a, however, it protrudes from the placing surface 811. Therefore, when a sample S is disposed across the positioning portions 812, the sample S is held in a state where it is placed over the recessed portions 812b of the positioning portions 812, and a gap is formed between the sample S and the placing surface 811.

The example shown in (b) in FIG. 8 shows a sample stage 82 formed by changing the shapes of the positioning portions 412 and the protrusion 712 of the sample stage 71 described above with reference to FIG. 7(a). FIG. 8(b) is a sectional view of the vicinity (vicinity of the center of the sample stage 81) of a protrusion 813 formed on the placing surface 821 of the sample stage 81. As shown in (b) in FIG. 8, the positioning portion 812 has a shape similar to that described in FIG. 8(a). The protrusion 813 is formed so that the height thereof becomes equal to that of the recessed portion 812b of the positioning portion 812 based on the placing surface 821. Therefore, when the sample S is disposed across the positioning portions 812, and placed over the protrusion 813, the sample S is held in a state where it is placed over the recessed portions 812b of the positioning portions 812 and the protrusion 813, and a gap is formed between the sample S and the placing surface 811.

The sample holder 40 of the present embodiment includes the sample stage 41 having the placing surface 411 formed so as to incline from a surface perpendicular to the optical axis L of excitation light, and includes an attaching flange 44 to be locked to the integrating sphere 20 so that the placing surface 411 is directed in a predetermined direction, so that a sample S placed on the placing surface 411 can be disposed at a predetermined angle with respect to the optical axis L of the excitation light. Therefore, the excitation light obliquely enters the sample S, and reflected light to be measured does not return to the excitation light introducing hole 201. The predetermined angle depends on the inclination of the placing surface 411, so that, for example, when a plurality of kinds of samples are measured by changing the predetermined angle, the measurement can be performed by changing the sample stage 41. The sample holder 40 is fixed by the attaching flange 44 so that the placing surface 411 is directed in a predetermined direction, so that light to be measured reflected by the sample S is irradiated always to a predetermined portion inside the integrating sphere 20, and errors of measured values can be reduced.

Subsequently, with reference to FIG. 2, a configuration of a photodetecting device 1 when the photodetecting device 1 is laid down (sideways) by positioning the placing surface 10b of the mount 10 downward so that the excitation light optical axis L is along the horizontal line, and measures a sample held by the sample holder 60, will be described. Here, the sample holder 60 is used mainly for measurement of a liquid sample in which a pigment, etc., is dissolved, and the sample is held by the sample holder 60 while being accommodated in a container such as an optical cell.

The positional relationship among the excitation light introducing hole 201, the sample introducing hole 202, and the photodetector introducing hole 203 is as described above. The sample introducing hole 205 (first sample introducing hole) is formed at one (the upper pole in FIG. 2) of the poles at which the integrating sphere 20 and the vertical line (the vertical line in the state of FIG. 2, that is, the perpendicular of the plane passing through the centers of the excitation light introducing hole 201, the sample introducing hole 202, and the photodetector introducing hole 203) intersect with each other. Into the sample introducing hole 205, the sample holder 60 is attached.

As described above, excitation light emitted from an excitation light source (not shown) is guided to the lens 302 of the optical fiber holder 30 for excitation light through an optical fiber (not shown). The excitation light is guided into the integrating sphere 20 along the optical axis L, and irradiated onto a solution sample inside the cell C held by the sample holder 60. The cell C is made of glass, and consists of a prismatic part and a branch tube connected to the prismatic part. In the present embodiment, the cell C is a glass square cell with an optical path length of 10 mm.

When the solution sample accommodated in the cell C is irradiated with the excitation light, light to be measured composed of a reflected component of the excitation light and a component generated from the solution sample which has absorbed the excitation light is generated. The light to be measured from the solution sample in the cell C irradiated with the excitation light is multiply diffused and reflected by a highly diffuse reflecting agent coated on the inner wall of the integrating sphere 20. The diffuse-reflected light to be measured enters the optical fiber 501 attached to the optical fiber holder 50 for photodetection. As described above, light to be measured which has entered the optical fiber 501 is guided to a photodetector which is not especially limited but, for example, a multi-channel photodetector (not shown) through the optical fiber 501. Measurement data detected by the multi-channel photodetector (not shown) is output to a data processor (not shown) and processed, and the intensity of the light to be measured is measured.

The sample holder 60 is removably attached to the integrating sphere 20 by the attaching flange 75 and the fixation screw 70. The mutual positional relationship between the attaching flange 75 and the integrating sphere 20 is determined by locking means such as a positioning pin. The mutual positional relationship between the attaching flange 75 and the sample holder 60 is also determined by locking means such as a positioning pin (locking part, positioning means). The attaching flange 75 is a ring-shaped flange. When the sample holder 60 is inserted into the ring and the fixation screw 70 screwed in a screw hole provided on the ring-shaped side surface portion is tightened, the sample holder 60 can be sandwiched and locked between the attaching flange 75 and the integrating sphere 20.

To the attaching flange 75, a cover 80 is attached with a fixation screw 85. The cover 80 is provided so as to cover the attaching flange 75, the sample holder 60, and the cell C held by the sample holder 60, and prevents ambient light from entering the inside of the integrating sphere from the outside.

Figure 9:
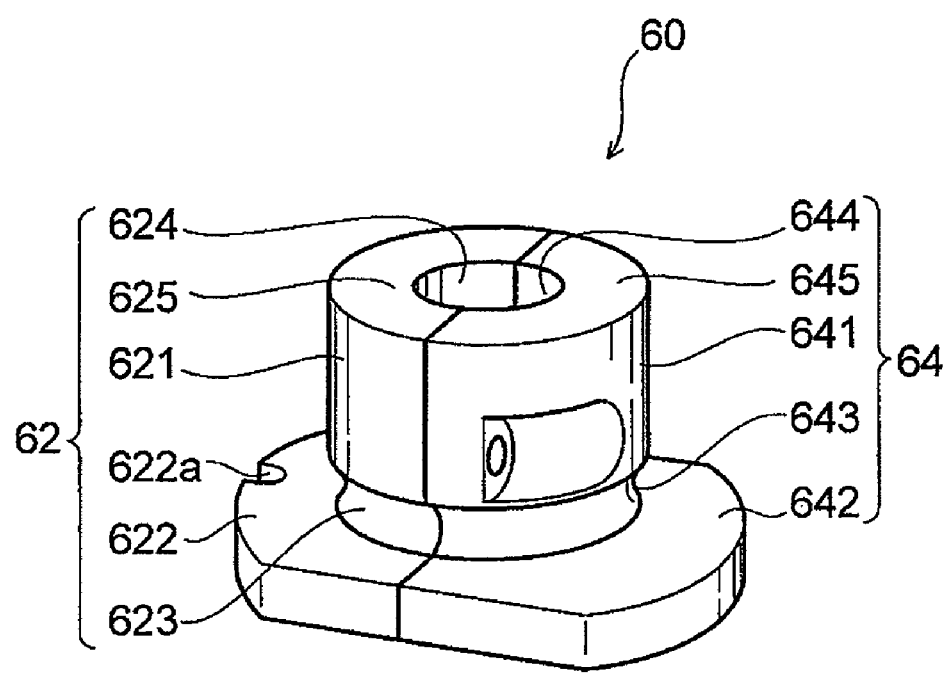
FIG. 9 is a perspective view of the sample holder of FIG. 2.

Subsequently, the sample holder 60 will be described in more detail with reference to FIG. 9. FIG. 9 is a perspective view of the sample holder 60. The sample holder 60 consists of two parts 62 and 64 having substantially the same shape.

The parts 62 and 64 include cylindrical parts 621 and 641 (holding parts) having substantially cylindrical shapes and flat plate parts 622 and 642 having substantially semicircular shapes partially cut, respectively. The flat plate part 622 is provided on one end of the cylindrical part 621 via a recessed part 623. Similarly, the flat plate part 642 is provided on one end of the cylindrical part 641 via a recessed part 643. The recessed parts 623 and 643 are provided along the outer peripheries of the cylindrical parts 621 and 641, respectively.

On portions which are opposed to each other when the part 62 and the part 64 are fitted to each other as the sample holder 60, a recessed portion 624 (grip portion) and a recessed portion 644 (grip portion) having semicircular sectional shapes are formed, respectively. The recessed portion 624 is formed from the flat plate part 622 to the other end of the cylindrical part 621 on the side opposite to the side of the flat plate part 622. Similarly, the recessed portion 644 is formed from the flat plate part 642 to the other end of the cylindrical part 641 on the side opposite to the side of the flat plate part 642. Therefore, when the part 62 and the part 64 are fitted to each other, the cell C can be inserted into the cylindrical hole formed by the recessed portion 624 and the recessed portion 644. On portions which come into contact with the cell C of the recessed portion 624 and the recessed portion 644 when the cell C is sandwiched between the part 62 and the part 64, a buffering member (not apparently shown in FIG. 3) is provided.

In the flat plate part 622 of the part 62, a notch 622a is formed. The notch 622a is formed at the substantially central portion on the outer periphery of the flat plate part 622. This notch 622a allows a positioning pin (not shown) formed on the attaching flange 75 to be inserted therein for positioning when the sample holder 60 is attached to the attaching flange 75.

The end faces 625 and 645 of the cylindrical parts 621 and 641 which are exposed inside the integrating sphere when the sample holder 60 is attached into the sample introducing hole 30 are preferably coated with a diffuse reflecting agent such as barium sulfate.

In the embodiment described above, optical measurement in which samples are separately held by the sample holders 40 and 60 according to the sample forms is described. When the sample holder 40 holds a sample, that is, when the sample on the placing surface 411 is measured by disposing the photodetecting device 1 (longitudinally) by positioning the placing surface 10a of the mount 10 downward as shown in FIG. 1, the sample holder 60 not holding the cell C is attached into the sample introducing hole 205, and the end faces 625 and 645 coated with a reflecting agent of the sample holder 60 diffuses and reflects the light to be measured as a part of the inner wall of the integrating sphere. When the sample holder 60 holds a sample, that is, when a sample inside the cell C is measured by laying down the photodetecting device 1 (sideways) by positioning the placing surface 10b of the mount 10 downward as shown in FIG. 2, the sample holder 40 not holding a sample is attached into the sample introducing hole 202, and the placing surface 411 coated with the reflecting agent of the sample holder 40 diffuses and reflects light to be measured as a part of the inner wall of the integrating sphere. Therefore, in the photodetecting device according to the present invention, the sample holders are selectively used according to the sample form, so that the troublesomeness of changing the integrating sphere is removed. Further, the regions (the end faces 625 and 645 and the placing surface 411) to be exposed inside the integrating sphere of the respective sample holders are coated with a light diffusing and reflecting agent, so that high-accuracy measurement can be performed.

Into the sample introducing hole which is not used for measurement, instead of the sample holder of the present invention, a cap (not shown) for preventing ambient light from entering the inside of the integrating sphere from the outside may be attached. The inside of the cap to be exposed inside the integrating sphere is preferably coated with a diffuse reflecting agent so as to function as a part of the inner wall of the integrating sphere.

Subsequently, a jig for sample holder will be described. A jig for a sample holder is for adjusting the relative positional relationship between the cell C to be introduced into the integrating sphere 20 for observing light to be measured generated according to irradiation of a sample with excitation light, and a sample holder 60 which is removably attached into the sample introducing hole 205 provided in the integrating sphere 20 and holds the cell C. This jig for sample holder is illustrated in FIG. 10.

Figure 10:
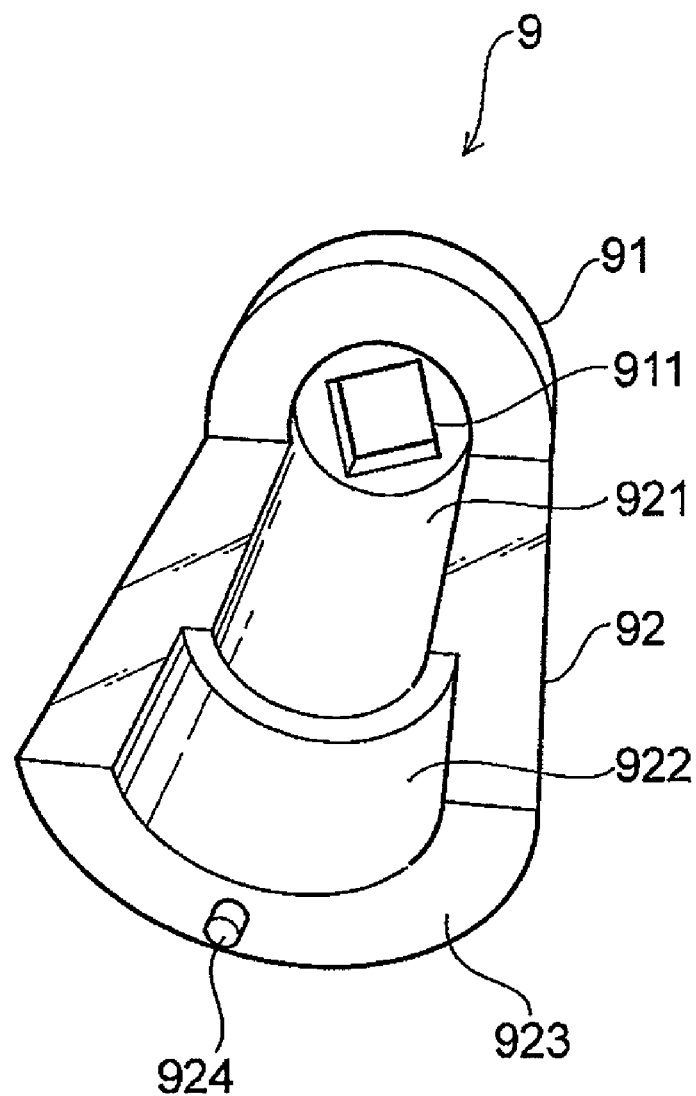
FIG. 10 is a perspective view of a jig for sample holder of the present embodiment.

As shown in FIG. 10, a jig 9 for a sample holder includes a main body part 92 extending along the cell C, a holder holding part 922 which is formed at the main body part 92 and holds the sample holder 60, and a cell holding part 91 which is formed at the main body part 92 and has a hole 911 (angle setting means) for directing the entrance surface of the cell C, when the excitation light enters the cell C, in a predetermined direction with respect to the sample holder 60.

The main body part 92 is a part having a semi-cylindrical shape extending along the cell C. On the inner side of the main body part 92, a holder holding groove 922 (holder holding part) extending from the end face 923 and a recess 921 which is linked to the holder holding groove 922 and extends to the cell holding part 91 are formed.

The holder holding groove 922 is a groove for holding the sample holder 60, and has a semicircular sectional shape, and is formed along the outer peripheries of the cylindrical parts 621 and 641 of the sample holder 60.

The sectional shape of the recess 921 is also semicircular, and the radius thereof is set to a radius which is smaller than that of the holder holding groove 922 and capable of accommodating the cell C. Therefore, when the cylindrical parts 621 and 641 of the sample holder 60 are accommodated in the holder holding groove 922, the flat plate parts 622 and 642 come into contact with the end face 923, and tip ends of the cylindrical parts 621 and 641 come into contact with the step portion between the holder holding groove 922 and the recess 921.

The cell holding part 91 is a semicircular flat plate part extending so as to intersect with the main body part 92. At the substantially central portion of the cell holding part 91, a hole 911 is formed. The hole 911 has substantially the same shape as the sectional shape of the cell C so as to allow the cell C to be inserted therein.

Figure 11:
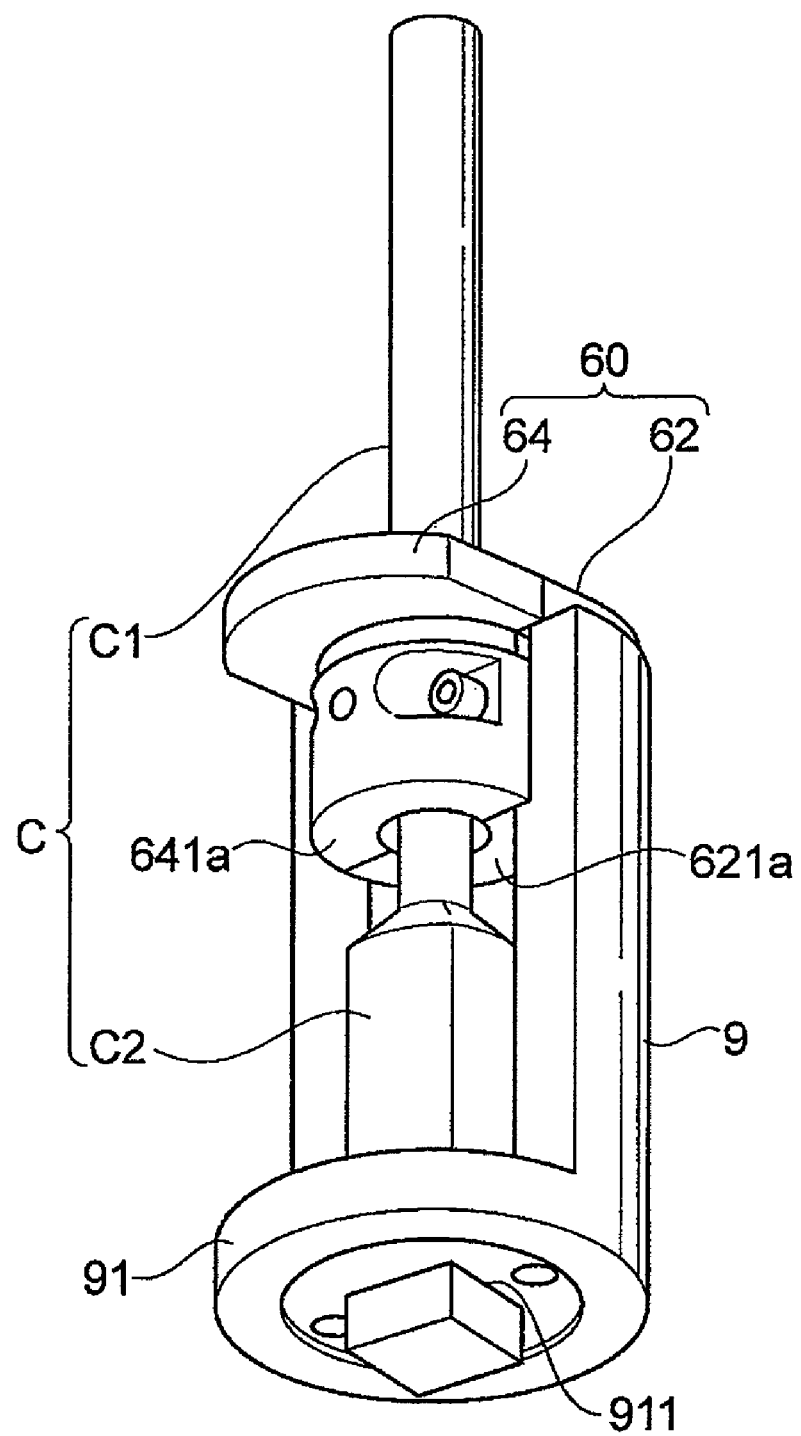
FIG. 11 is a view for describing a method for using the jig for sample holder of FIG. 10.

Herein, a state where the jig 9 for sample holder is made to hold the sample holder 60 and the cell C is shown in FIG. 11. A method for using the jig 9 for sample holder will be described with reference to FIG. 11.

First, the branch tube C1 of the cell C is sandwiched and held between the part 62 and the part 64 of the sample holder 60, and the part 62 and the part 64 are temporarily fastened by a screw. At this time, the branch tube C1 is sandwiched between the recessed portion 624 of the part 62 and the recessed portion 644 of the part 64.

Subsequently, an assembly consisting of the sample holder 60 and the cell C thus temporarily fastened is attached to the jig 9 for sample holder. In detail, the prism part C2 of the cell C is accommodated in the recess 921 formed in the cell holding part 91. Further, the sample holder 60 is accommodated in the holder holding part 922, and the positioning pin 924 of the jig 9 for sample holder is inserted in the notch 622a of the sample holder 60.

Subsequently, the screw which temporarily fastens the part 62 and the part 64 is loosened, the vertical position of the cell C is adjusted, and the prismatic part C2 of the cell C is inserted into the hole 911. The hole 911 into which the prismatic part C2 of the cell C is inserted has substantially the same shape as the sectional shape of the prism part C2, so that the cell C is movable vertically.

In the case of the disposition shown in FIG. 11, the hole 911 is formed so that the cell C has an appropriate angle with respect to the sample holder 60. In the case of the present embodiment, setting is made so that the angle between the optical axis L of excitation light and the entrance surface of the prismatic part C2 of the cell C becomes 15° when the sample holder 60 holding the cell C is attached to the integrating sphere 20.

After positioning is finished, the part 62 and the part 64 are fixed with a screw. The cell C and the sample holder 60 thus fixed to each other is attached to the photodetecting device 1 as shown in FIG. 2, and irradiated with excitation light.

Figure 12:
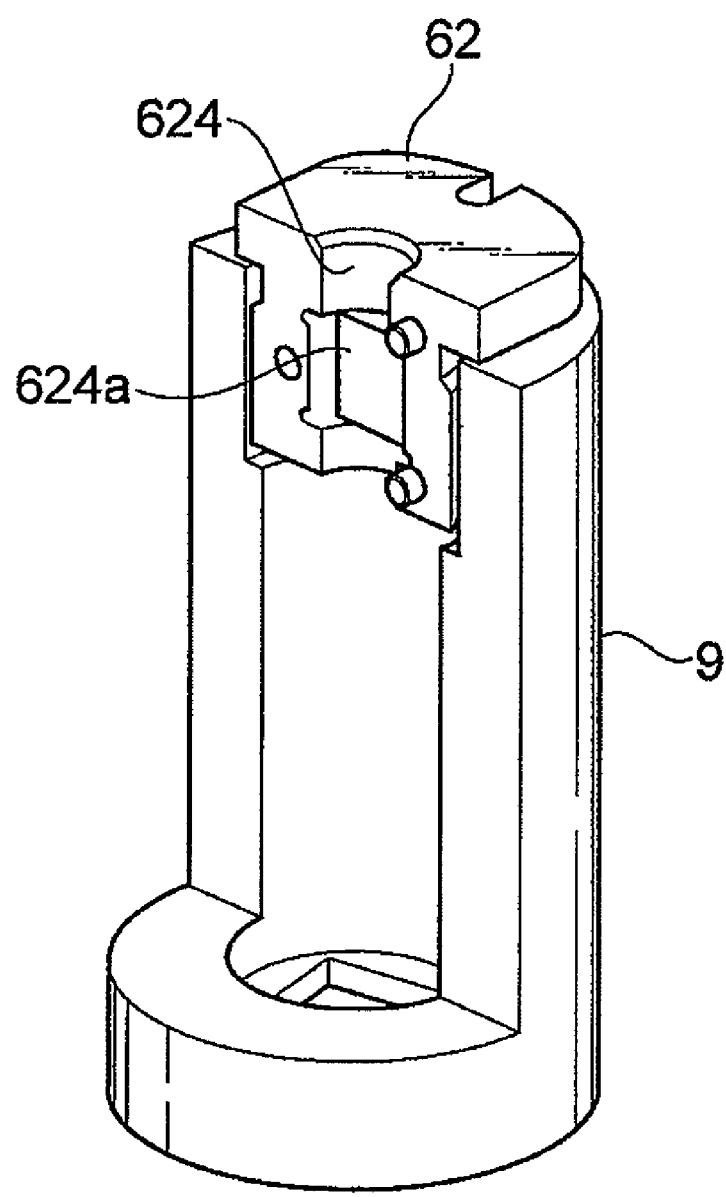
FIG. 12 is a view for describing the sample holder and the jig for sample holder of the present embodiment.

Here, a state where the screw fixing the part 62 and the part 64 is removed and the part 64 and the cell C are removed from the state of FIG. 11 is shown in FIG. 12. As shown in FIG. 12, the buffering member 624a is disposed in the recessed portion 624 of the part 62 in which the branch tube C1 of the cell C is held. Therefore, even when the part 62 and the part 64 are fixed with a screw while sandwiching the branch tube C1 of the cell C, the buffering member 624a acts to be able to suppress the cell C from being damaged, and suppress sliding of the cell C.

It is also preferable that the tip end face 621a of the part 62 and the tip end face 641a of the part 64 of the sample holder 60 are coated with a reflecting material, respectively.

Figure 13:
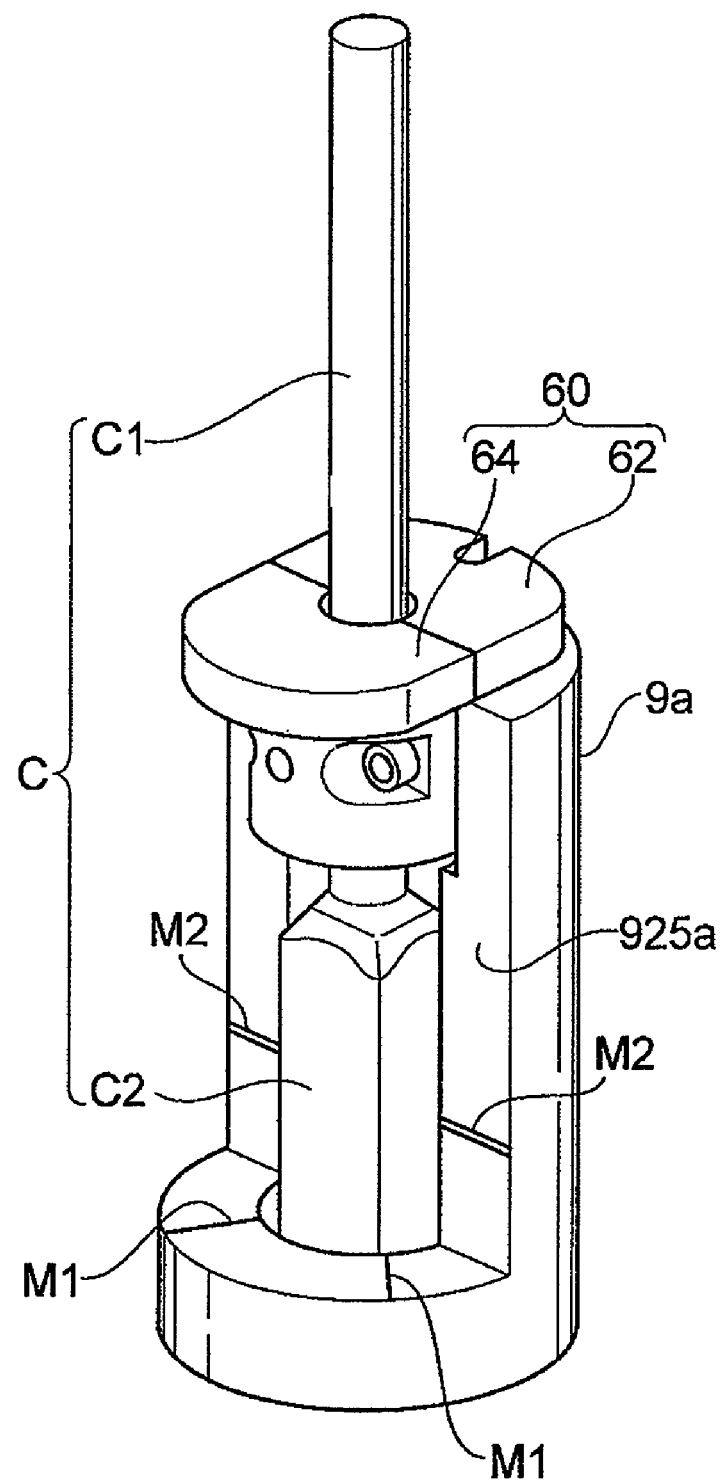
FIG. 13 is a perspective view of a jig for sample holder of an exemplary variation of the present embodiment.
Figure 14:
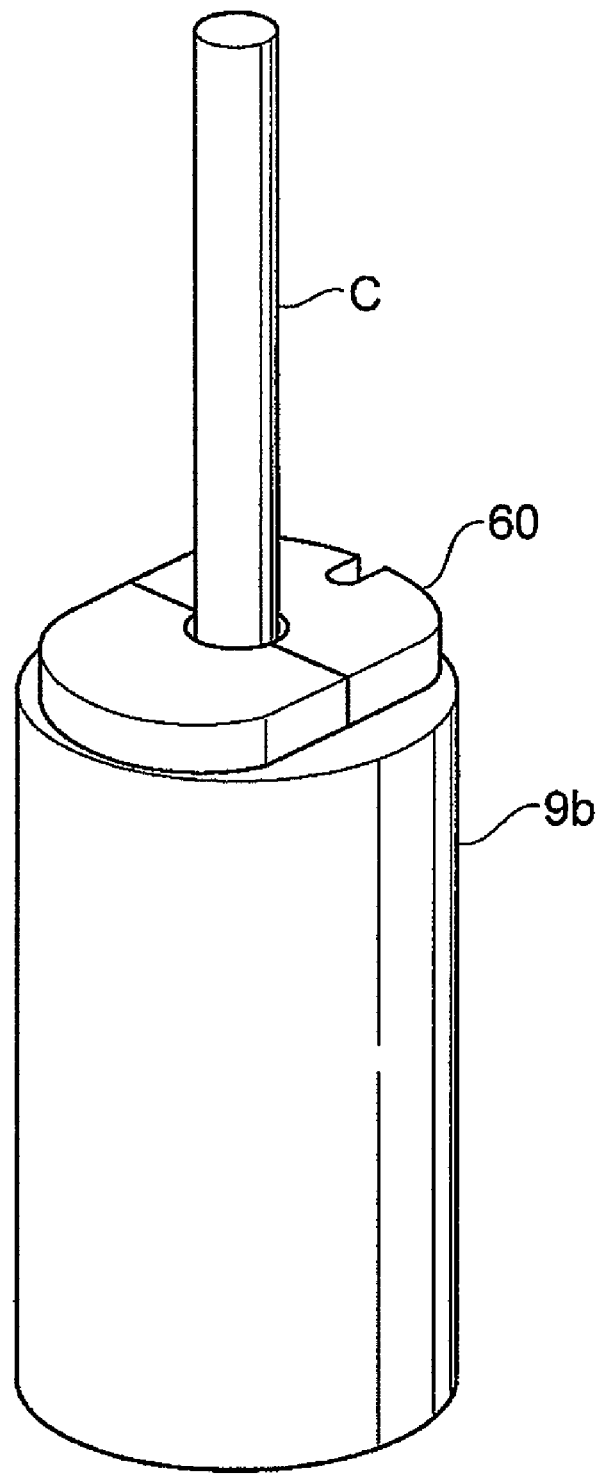
FIG. 14 is a perspective view of a jig for sample holder of an exemplary variation of the present embodiment.

Exemplary variations of the present embodiment are shown in FIG. 13 and FIG. 14. The exemplary variation show in FIG. 13 shows a jig 9a for sample holder in which marks M1 are provided on two points of the cell holding part 91 instead of the hole 911 as angle setting means. The marks M1 are provided at predetermined positions at which the cell C is visible.

First, the cell C and the sample holder 60 being temporarily fastened are attached to the jig 9a for sample holder in the same manner as described above. Subsequently, the screw temporarily fastening the part 62 and the part 64 is loosened, and the cell C is rotated so that the angles of the prismatic part C2 of the cell C match the marks M1. The marks M1 are formed so that the cell C has an appropriate angle with respect to the sample holder 60. When positioning of the cell C is completed, the part 62 and the part 64 are fastened and fixed with a screw.

In the exemplary variation shown in FIG. 13, marks M2 as height adjusting means are also provided. The marks M2 are for matching the position of the optical axis L of excitation light inside the integrating sphere 20 and the entrance position of the excitation light on the cell C. The reason for performing this height adjustment is that the quantum yield is measured for a reference sample, and the height, angle, and liquid level, etc., need to become equal between the reference sample and the measurement sample.

The exemplary variation shown in FIG. 14 is a jig 9b for a sample holder which includes a main body having a columnar shape. When the jig 9b for sample holder is used, the positional relationship with the sample holder 60 can be adjusted while the cell C is left covered.

Other than the above-described prism-shaped cell, any cell is preferably applicable as long as the excitation light entrance surface and exit surface are parallel to each other. Further, a cell such as a tube cell and a cylindrical cell can also be used.

A function and effect of the present embodiment will be described. The prismatic part C2 of the cell C can be directed in a predetermined direction and attached to the sample holder 60. When the sample holder 60 and the cell C thus assembled are attached to the integrating sphere 20, they can be attached so that a predetermined angle (for example, 15°) is formed between the optical axis L of the excitation light and the entrance surface of the cell C. The reproducibility of this attaching angle is also improved, so that the measurement accuracies of reference measurement and sample measurement can be more effectively improved.

The entrance surface of the cell C is a glass plate and is optically flat, and the entrance surface reflects a part of the light which enters the entrance surface to the side opposite to the entrance direction, and therefore, for example, when the entrance surface is disposed so as to become perpendicular to the optical axis L of the excitation light, light reflected by the entrance surface returns to the excitation light introducing hole 201, and the intensity of the light to be measured cannot be accurately measured. Therefore, as in the case of the present embodiment, by disposing the cell C at a predetermined angle with respect to the optical axis L of the excitation light, the reflected light can be suppressed from returning to the excitation light introducing hole 201, and can be made to irradiate the inner wall of the integrating sphere 20.

When the cell C is held by the sample holder 60 as in the case of the present embodiment, only the portion of the branch tube of the cell C is held, so that the influence on the light to be measured can be reduced.

Further, measurement can be performed by selectively using the sample holder 40 suitable for a sample such as powder and a thin film and the sample holder 60 and the cell C suitable for a solution sample, so that various samples can be measured with one integrating sphere 20.

The invention claimed is:

1. A photodetecting device comprising: an integrating element having a spherical inner wall and configured to observe light to be measured generated according to irradiation of a sample with excitation light; and a sample holder to be removably attached to the integrating element, wherein the integrating element has an excitation light introducing hole for introducing excitation light and a sample introducing hole for introducing a cell held by the sample holder, the cell has a prismatic part, and a branch tube connected to the prismatic part, and the sample holder is locked to the sample introducing hole, and has a holding part which holds the branch tube of the cell for accommodating the sample and positioning means for disposing the cell with the branch tube has an axis so that an entrance surface of the cell, through which the excitation light enters the cell, and an exit surface of the cell parallel to the entrance surface incline relative to a surface perpendicular to the optical axis of the excitation light.

2. The photodetecting device according to claim 1, wherein the holding part includes a grip portion for gripping the cell, and the grip portion includes a buffering member at a portion which comes into contact with the cell.

3. The photodetecting device according to claim 1, wherein the positioning means is a locking part for locking the sample holder to the integrating element.

4. The photodetecting device according to claim 1, further comprising: a jig for sample holder for adjusting a relative positional relationship between the cell and the sample holder, including:
 a main body part extending along the cell;
 a holder holding part which is formed at the main body part and holds the sample holder; and
 angle setting means which is formed at the main body part and directs the entrance surface of the cell, through which the excitation light enters the cell, in a predetermined direction with respect to the sample holder.

5. The photodetecting device according to claim 4, wherein the angle setting means is a hole having substantially the same shape as the sectional shape of the cell, formed at a cell holding part extending so as to intersect with the main body part.

6. The photodetecting device according to claim 4, wherein the angle setting means is a mark provided at a predetermined position at which the cell is visible.

7. The photodetecting device according to claim 4, further comprising height adjusting means for matching the position of the optical axis of the excitation light inside the integrating element and the entrance position of the excitation light on the cell.

8. A photodetecting device comprising: an integrating sphere for observing light to be measured generated according to irradiation of a sample with excitation light; and a sample holder to be removably attached to the integrating sphere, wherein
 the integrating sphere has an excitation light introducing hole for introducing excitation light; a first sample introducing hole for introducing a first sample holder; a second sample introducing hole for introducing a second sample holder; and a photodetector introducing hole,
 the first sample holder has a holding part which holds a cell for accommodating a sample; and a first locking part for locking the first sample holder to the integrating sphere,
 the second sample holder has a sample stage onto which a sample is placed; and a second locking part for locking the second sample holder to the integrating sphere,
 the first sample introducing hole is formed at a position on a first meridian having poles set at a position at which the excitation light introducing hole is formed and a position at which the second sample introducing hole is formed, and at distances substantially equal to each other from the poles of the first meridian,
 the photodetector introducing hole is formed at a position on a second meridian having poles set at the position at which the excitation light introducing hole is formed and the position at which the second sample introducing hole is formed, and at distances substantially equal to each other from the poles of the second meridian, and
 the second meridian is perpendicular to the first meridian at the position at which the excitation light introducing hole is formed.

9. The photodetecting device according to claim 8, wherein the first locking part has positioning means for disposing the cell so that an entrance surface of the cell, through which the excitation light enters the cell, inclines relative to a surface perpendicular to the optical axis of the excitation light.

10. The photodetecting device according to claim 8, wherein
 a placing surface on which the sample is placed is formed on the sample stage so as to incline relative to a surface perpendicular to the optical axis of the excitation light, and
 the second locking part locks the second sample holder to the integrating sphere so that the placing surface is directed in a predetermined direction inside the integrating sphere.

11. The photodetecting device according to claim 8, wherein a portion to be exposed inside the integrating sphere of at least one of the first sample holder and the second sample holder is a diffuse reflecting surface.

12. The photodetecting device according to claim 8, wherein the integrating sphere is attached to an L-shaped mount having two placing surfaces.

13. The photodetecting device according to claim 1, wherein the integrating element is an integrating sphere.

\* \* \* \* \*